US012648940B2

(12) United States Patent
Crivaro et al.

(10) Patent No.: US 12,648,940 B2
(45) Date of Patent: Jun. 9, 2026

(54) BUPIVACAINE LIQUID FORMULATIONS

(71) Applicant: FRESENIUS KABI AUSTRIA GMBH, Graz (AT)

(72) Inventors: Claudio Crivaro, Graz (AT); Christian Masser, Graz (AT); Theofanis Mantourlias, Mainz (DE)

(73) Assignee: Fresenius Kabi Austria GmbH, Graz (AT)

( * ) Notice: Subject to any disclaimer, the term of this patent is extended or adjusted under 35 U.S.C. 154(b) by 0 days.

(21) Appl. No.: 18/465,893

(22) Filed: Sep. 12, 2023

(65) Prior Publication Data

US 2025/0082622 A1 Mar. 13, 2025

(51) Int. Cl.
*A61K 31/445* (2006.01)
*A61J 1/14* (2023.01)
*A61K 47/02* (2006.01)

(52) U.S. Cl.
CPC ............ *A61K 31/445* (2013.01); *A61K 47/02* (2013.01); *A61J 1/1468* (2015.05)

(58) Field of Classification Search
CPC ...... A61K 31/445; A61K 9/08; A61K 9/0019; A61J 1/10
See application file for complete search history.

(56) References Cited

U.S. PATENT DOCUMENTS

| | | | |
|---|---|---|---|
| 6,284,805 | B1 | 9/2001 | Brown |
| 2003/0133986 | A1 | 7/2003 | Tsao |
| 2019/0070157 | A1 | 3/2019 | Joshi et al. |

FOREIGN PATENT DOCUMENTS

| | | | | |
|---|---|---|---|---|
| CN | 102311586 | A * | 1/2012 | ............. B29C 47/92 |
| EP | 1708722 | B1 | 5/2014 | |
| WO | 2007/073397 | A1 | 6/2007 | |
| WO | 2017/193066 | A1 | 11/2017 | |
| WO | 2021/216928 | A1 | 10/2021 | |
| WO | 2022/221534 | A1 | 10/2022 | |
| WO | WO-2022212166 | A1 * | 10/2022 | ........... A61K 31/167 |
| WO | 2025/015011 | A1 | 1/2025 | |

OTHER PUBLICATIONS

CN102311586A; 2012; English machine translation relied on suppled by Google patents; https://patent.google.com/patent/CN102311586A/en; accessed Feb. 9, 2024 (Year: 2012).*

Upton et al; "The Relationship Between Some Physicochemical Properties of Ionisable Drugs and Their Sorption into Medical Plastics"; 1987; Aust. J. Hops. Pharm.; 17(4): 267-270 (Year: 1987).*

Medthority; "Bupivacaine Hydrochloride 0.125%w/v Solution for Infusion"; Apr. 7, 2022 (last updated); https://www.medthority.com/drugs/n-nervous-system/n01/n01b/n01bb/n01bb01/bupivacaine-hydrochloride-02.125wv-solution-for-infusion/; accessed Feb. 9, 2024 (Year: 2022).*

Jones et al.; "Stability of bupivacaine hydrochloride in polypropylene syringes"; 1993; Am. J. Hosp. Pharm.; 50: 2364-5 (Year: 1993).*

Fresenius Kabi USA, "Prescribing Information for Sensorcainetm bupivacaine HCI injection," Revised Nov. 2022 (2 pgs + enlargement = 27 pgs.) https://www.myfreseniuskabi.com/medias/US-PH-Sensorcaine-FK-451106J- PI.pdf?context=bWFzdGVyfHBkZnN8NDMxMic4fGFwcGxpY2F0aW9uL3BkZnxhR0V3TDJnMFpDODVPRGMOTnpJMk1ERTNNRFUwTDFWVExWQkIMVK5sYm5OdmNtTmhhVzVsTFVaTExUUTFNVEV3TmtvdFVPa3ViR1jtfDZIYiQ1MiY1MzA1Mz g3ZDg5ZGNINmRhMik0NmVINWUzNTE3YzZkZmZiYiBiYilMDZmYmQ1MzQSZmESMzgyYzU.

Da Poiam et al., "Adrenalina, Esterilização, pH e Dissociação dos Anestésicos Locais," *Rev. Bras Anest* 33(1): 023-025 (1983) downloaded Sep. 6, 2023 from https://bian- sba.org/article/519c9dad8e6f1a40018b460d/pdf/rba-33-1-23.pdf.

Fargon Sterile Services, US Product Catalog (Apr. 2023)—11 pgs. Downloaded Sep. 6, 2023 https://fagroncdcvid365cedata.blob.core.windows.net/publicvisiblemarketingfiles/FSS_MSL_All_Products.PDF.

Fresenius Kabi USA, "Prescribing Information for Sensorcaine™ bupivacaine HCI injection," Revised Nov. 2022 (2 pgs) https://www.myfreseniuskabi.com/medias/US-PH-Sensorcaine-FK-451106J-PI.pdf?context=bWFzdGVyfHBkZnN8NDMxMic4fGFwcGxpY2F0aW9uL3BKZnxhR0V3TDJnMFpDODVPRGMOTnpJMk1ERTNNRFUwTDFWWExWQkIMVk5sYm5OdmNtTmhhVzVsTFVaTExUUTFNVEV3TmtvdFVFa3VIR1JtfDZIYiQ1MiY1MzA1Mzg3ZDg5ZGNiNmRhMik0NmVINWUzNTE3YzZkZmZiYiBiYIl1MDZmYmQ1MzQ5ZmE5MzgyYzU.

Hospira Inc., "Prescribing Information for MARCAINE™ bupivacaine HCI injection," Revised Mar. 2023 (21 pgs.) https:/labeling.pfizer.com/ShowLabeling.aspx?id=4373.

Jones et al., "Stability of Bupivacaine Hydrochloride in Polypropylene Syringes" *Am J Hosp Pharm*, 50: 2364-5 (1993).

Mcmorland et al., "Effect of pH-adjustment of bupivacaine on onset and duration of epidural analgesia in parturients," *Can Anaesth Soc J*, 33(5): 537-541 (1986).

QuVa Pharma, 2023 Product Catalog (21 pgs.) Downloaded Sep. 6, 2023 https://quvadev.blob.core.windows.net/web-attachments/QuVa%20Documents/QuVaPharma-Product%20Catalog.pdf.

Sintetica GmbH, "Summary of Product Characteristics for Bupivacaine Hydrochloride 0.1% w/v Solution for Infusion," Updated May 9, 2023 (7 pgs.).

Upton et al., "The Relationship Between Some Physicochemical Properties of Ionisable Drugs and Their Sorption into Medical Plastics," *Australian Journal of Hospital Pharmacy*, 17(4): 267-270 (1987).

Anonymous, "Public Assessment Report—Scientific Discussion. Levobupivacaine Fresenius Kabi 0.625 mg/ml and 1.25 mg/ml, solution for infusion Levobupivacaine Fresenius Kabi 2.5 mg/ml, 5 mg/ml and 7.5 mg/ml, solution for injection/infusion," (Oct. 2014), (10 pgs.) XP093230721, Retrieved from the Internet: URL: https://www.geneesmiddeleninformatiebank.nl/pars/h113448.pdf [retrieved on Dec. 11, 2024].

(Continued)

*Primary Examiner* — Timothy P Thomas

(74) *Attorney, Agent, or Firm* — Leydig, Voit & Mayer, Ltd.

(57) ABSTRACT

The invention provides a liquid formulation comprising bupivacaine or a pharmaceutically acceptable salt thereof, a method for preparing the formulation, and a product which includes the formulation. The formulation of the invention may include a tonicity agent, and has an initial pH of from about 4.2 to about 4.5. The formulation of the invention is stable and ready-to-administer.

6 Claims, No Drawings

(56) References Cited

OTHER PUBLICATIONS

Anonymous, "Summary of Product Characteristics Levobupivacaine 1.25 mg/ml solution for infusion," (May 2021), Health Products Regulatory Authority (HPRA), Dublin, Ireland, (9 pgs.) XP093230722, Retrieved from the Internet: URL: https://www.hpra.ie/img/uploaded/swedocuments/Licence_PA2059-009-002_18052021115309.pdf [retrieved on Dec. 3, 2024].

Priston et al., "Stability of an epidural analgesic admixture containing epinephrine, fentanyl and bupivacaine," Anaesthesia 59(10): 979-983 (2004), Blackwell Science Ltd, GB, XP071021473, ISSN: 0003-2409, DOI: 10.1111/J.1365-2044.2004.03803.X.

European Patent Office, International Search Report in International Application No. PCT/IB2024/058897 (Jan. 7, 2025).

* cited by examiner

BUPIVACAINE LIQUID FORMULATIONS

BACKGROUND OF THE INVENTION

Bupivacaine is a local anesthetic that binds to sodium ion channels in the neuronal membrane, resulting in a decrease in sodium influx into nerve cells, which prevents depolarization and nerve impulse conduction. Bupivacaine, also referred to as 1-butyl-N-(2,6-dimethylphenyl)piperidine-2-carboxamide, has a pKa of approximately 8.1, a molecular weight of approximately 288.4 g/mol, and the following chemical structure:

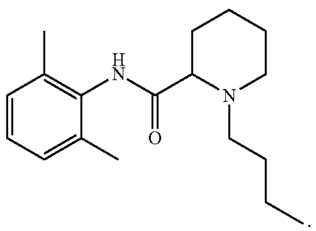 [SMILES: CCCCN1CCCCC1C(=O)Nc1c(C)cccc1C]

In medicine, injections of bupivacaine are indicated for production of local or regional anesthesia or analgesia for surgery, diagnostic and therapeutic procedures, and for obstetrical procedures. FDA-approved injection solutions containing bupivacaine with and without epinephrine are available under the trade names SENSORCAINE™ and MARCAINE™ and in generic form from several manufacturers.

SENSORCAINE™ is provided in single- and multiple-dose glass vials as a sterile isotonic aqueous solution containing 2.5 mg/mL, 5.0 mg/mL, or 7.5 mg/mL bupivacaine HCl and sodium chloride, adjusted to pH between 4.0 and 6.5 with sodium hydroxide and/or hydrochloric acid, and further including 1 mg/mL methylparaben as preservative in the multiple dose vials. SENSORCAINE™ also is provided in single- and multiple-dose glass vials as a sterile isotonic aqueous solution containing 2.5 mg/mL, 5.0 mg/mL, or 7.5 mg/mL bupivacaine HCl, 0.005 mg/mL epinephrine (as bitartrate), 0.5 mg/mL sodium metabisulfite, 0.2 mg/mL citric acid (anhydrous), and sodium chloride, adjusted to pH between 3.3 and 5.5 with sodium hydroxide and/or hydrochloric acid, and further including 1 mg/mL methylparaben as preservative in the multiple dose vials.

MARCAINE™ is provided in single- and multiple-dose glass vials as a sterile isotonic aqueous solution containing 2.5 mg/mL, 5.0 mg/mL, or 7.5 mg/mL bupivacaine HCl and sodium chloride, adjusted to pH between 4.0 and 6.5 with sodium hydroxide and/or hydrochloric acid, and further including 1 mg/mL methylparaben as preservative in the multiple-dose vials. MARCAINE™ also is provided in single- and multiple-dose glass vials as a sterile isotonic aqueous solution containing, per mL, 2.5 mg or 5.0 mg bupivacaine HCl, 0.005 mg epinephrine (as bitartrate), 0.5 mg sodium metabisulfite, 0.001 mL monothioglycerol and 2 mg ascorbic acid as antioxidants, 0.0017 mL of 60% sodium lactate buffer, 0.1 mg edetate calcium disodium as stabilizer, and sodium chloride, adjusted to pH between 3.4 and 4.5 with sodium hydroxide and/or hydrochloric acid, and further including 1 mg methylparaben as preservative in the multiple-dose vials.

A bupivacaine infusion solution is available from Sintetica Limited outside of the U.S. provided in 100- or 250-mL polypropylene infusion bags containing 0.1% w/v bupivacaine HCl, sodium chloride, sodium hydroxide, and water for injection having a pH range of 4.0-6.5. The Summary of Product Characteristics (SMPC) indicates that this product should not be stored above 25° C. and has a shelf life of 2 years.

Injection solutions containing bupivacaine optionally including at least one other active pharmaceutical ingredient (API) also are available from compounding pharmacies as sterile-to-sterile or API-to-sterile products supplied in bags, syringes, or cassette reservoirs. Injection solutions supplied by compounding pharmacies generally have a shelf life of 30-180 days.

There remains a need in the art for improved ready-to-administer, injectable formulations of bupivacaine which are storage stable, preferably for longer durations at room temperature.

BRIEF SUMMARY OF THE INVENTION

The invention provides a ready-to-administer, liquid formulation comprising a pharmaceutically effective amount of bupivacaine or a pharmaceutically acceptable salt thereof, a tonicity agent, and water, wherein the formulation has an initial pH of from about 4.2 to about 4.5, and wherein the formulation is stable for at least about 12 months at room temperature.

The invention also provides a method for preparing a ready-to-administer, liquid bupivacaine formulation that is stable for at least about 12 months at room temperature. The method comprises dissolving a pharmaceutically effective amount of bupivacaine or a pharmaceutically acceptable salt thereof and a tonicity agent in water to form a first solution, adjusting the first solution to a pH of from about 4.2 to about 4.5 to form a second solution, and sterilizing the second solution to provide the ready-to-administer, liquid bupivacaine formulation.

DETAILED DESCRIPTION OF THE INVENTION

The invention provides an aqueous liquid formulation comprising a pharmaceutically effective amount of bupivacaine or a pharmaceutically acceptable salt thereof and a tonicity agent, wherein the formulation has an initial pH of from about 4.2 to about 4.5, and wherein the pH drift of the formulation is less than about 0.4 pH units following terminal sterilization. The liquid formulation according to the invention is ready-to-administer and has a shelf life of at least about 12 months.

As used herein, a "ready-to-administer" formulation refers to a sterile, injectable formulation that need not be reconstituted from a solid or diluted from a concentrated solution by a healthcare provider prior to use. Rather, in the context of bupivacaine formulations of the invention, a ready-to-administer formulation is supplied by a pharmaceutical manufacturer as a liquid having a pharmaceutically effective amount of bupivacaine dissolved therein and may be contained within a suitable container (e.g., a bag or bottle) along with instructions indicating that no further dilution prior to injection or infusion is required. The ready-to-administer formulation of the invention also may be referred to as "premix", "premixed", or "premixture", which distinguishes the formulation of the invention from other ready-to-administer formulations that require sterile-to-sterile compounding or API-to-sterile compounding prior to administration, and typically have a shelf life of 180 days or less, e.g., 90 days or less, 45 days or less, or 30 days or less.

The formulation according to the present invention is stable. As used herein, the terms "stable" and "stability" encompass any characteristic of the formulation which may change or be affected by storage conditions including, without limitation, potency, total impurities, bupivacaine degradation products, specific optical rotation, optical purity, appearance, viscosity, sterility, particulates (visible and subvisible), color, and/or clarity. The storage conditions which may affect stability may include, for example, duration, temperature, humidity, and/or light exposure.

For example, a stable bupivacaine formulation may refer to a formulation that contains at least about 90%, e.g., least about 95%, at least about 96%, at least about 97%, or at least about 98%, of the labeled concentration of bupivacaine or pharmaceutically acceptable salt thereof after storage at room temperature (e.g., 250° C.±2° C./60% relative humidity (RH)±5% RH) and/or under accelerated conditions (e.g., at 40° C.±2° C./75% RH±5% RH). A stable bupivacaine formulation also may refer to a formulation that contains less than about 110%, e.g., less than about 105%, less than about 104%, less than about 103%, or less than about 102%, of the of the labeled concentration of bupivacaine or pharmaceutically acceptable salt thereof after storage at room temperature and/or under accelerated conditions. A stable bupivacaine formulation additionally may refer to a formulation that contains from about 95% to about 105%, e.g., from about 96% to about 104%, from about 97% to about 103%, from about 98% to about 102%, or from about 99% to about 101%, of the labeled concentration of bupivacaine or pharmaceutically acceptable salt thereof after storage at room temperature and/or under accelerated conditions.

A stable bupivacaine formulation also may refer to a formulation that contains less than about 5% (area percent), e.g., less than about 4%, less than about 3%, less than about 2%, less than about 1%, less than about 0.5%, less than about 0.25%, less than about 0.1%, or less than 0.05%, of total bupivacaine-related impurities present in the formulation after storage at room temperature and/or under accelerated conditions. A stable bupivacaine formulation also may refer to a formulation that contains from about 0.05% to about 5%, e.g., from about 0.1% to about 4%, from about 0.5% to about 3%, from about 0.25% to about 2%, from about 0.1% to about 1%, from about 0.05% to about 0.5%, or from about 0.05% to about 0.25%, of total bupivacaine-related impurities present in the formulation after storage at room temperature and/or under accelerated conditions.

A stable bupivacaine formulation also may refer to a formulation that contains less than about 2% (area percent), e.g., less than about 1%, less than about 0.5%, less than about 0.25%, less than about 0.1%, less than about 0.05%, less than about 0.025%, or less than about 0.01%, of any individual bupivacaine-related impurity present in the formulation after storage at room temperature and/or under accelerated conditions. A stable bupivacaine formulation additionally may refer to a formulation that contains about 0.01% to about 2%, about 0.01% to about 1%, about 0.01% to about 0.5%, about 0.025% to about 0.25%, about 0.05% to about 0.5%, or about 0.05% to about 0.25% of any individual bupivacaine-related impurity present in the formulation after storage at room temperature and/or under accelerated conditions.

In some embodiments, the bupivacaine formulation of the invention is stable for at least about 9 months, e.g., at least about 12 months, at least about 18 months, at least about 24 months, or at least about 36 months at room temperature (e.g., at 25±2° C./60% RH±5% RH) or at refrigerated temperature (e.g., at 5±3° C.). The invention also includes embodiments in which the bupivacaine formulation of the invention is stable for at least about 1 month, e.g., at least about 3 months, at least about 6 months, or at least about 12 months under accelerated conditions (e.g., at 400° C.±2° C./75% RH±5% RH).

Methods for determining the stability of a formulation of the invention with respect to a given parameter are well-known in the art. For example, individual impurities and total impurities may be assessed by high-performance liquid chromatography (HPLC) or thin layer chromatography (TLC). Unless indicated otherwise, a percentage amount bupivacaine, any individual impurity, or total impurities reported herein in the formulation is determined by a peak area percent method using HPLC.

In some embodiments, a stable bupivacaine formulation may refer to a formulation that is colorless after storage under room temperature and/or accelerated conditions. The color of the formulation may be determined, for example, by a United States Pharmacopoeia (USP) or a European Pharmacopoeia (Ph. Eur.) color method. For example, a stable bupivacaine formulation of the invention may refer to a formulation that has a coloration of not less than B8 as determined by Ph. Eur. Method 2.2.2 after storage for at least 6 months at room temperature. By way of further example, a stable bupivacaine formulation of the invention may refer to a formulation that has a coloration of not less than B8 as determined by Ph. Eur. Method 2.2.2 after storage for at least 1 month under accelerated conditions (e.g., at 400° C.±2° C./75% RH±5% RH).

The formulation may include a therapeutically effective amount of bupivacaine or a pharmaceutically acceptable salt thereof, such as, e.g., bupivacaine HCl. Preferably, the bupivacaine is an approximately equimolar mixture of R(+) bupivacaine and S(−) bupivacaine. However, in some embodiments, the bupivacaine is enantiomerically pure, e.g., at least about 95% S-isomer (levobupivacaine). The bupivacaine or pharmaceutically acceptable salt thereof in the formulation of the invention may be at a concentration of from about 0.1 mg/mL to about 10 mg/mL, e.g., about 0.1 mg/mL to about 5 mg/mL, about 0.2 mg/mL to about 2 mg/mL, about 0.5 mg/mL to about 1.5 mg/mL, or about 0.6 mg/mL to about 1.3 mg/mL. In some embodiments, the formulation includes about 0.625 mg/mL bupivacaine or a pharmaceutically acceptable salt thereof. In other embodiments, the formulation includes about 1.25 mg/mL bupivacaine or a pharmaceutically acceptable salt thereof.

The formulation may be provided in any suitable volume. In some embodiments, the volume of the formulation is about 5 mL or more, e.g., about 10 mL or more, about 50 mL or more, about 100 mL or more, about 150 mL or more, about 200 mL or more, or about 250 mL or more. In other embodiments, the volume of the formulation is about 1 L or less, e.g., about 750 mL or less, about 500 mL or less, about 400 mL or less, about 300 mL or less, about 250 mL or less, or about 200 mL or less. The formulation also may be provided in a volume bounded by any two of the aforementioned endpoints. For example, the formulation may be provided in a volume of from about 10 mL to about 200 mL, from about 50 mL to about 500 mL, from about 100 mL to about 400 mL, from about 150 mL to about 300 mL, or from about 200 mL to about 300 mL. In certain embodiments, the volume of the formulation is about 250 mL. One of ordinary skill in the art may readily select an appropriate container based upon the volume of the formulation.

The present invention is based, at least in part, on the surprising and unexpected discovery that the pH of an aqueous bupivacaine formulation provided in a plastic container drops following thermal sterilization, and that the magnitude of the pH drop is related to the initial pH of the formulation. While not wishing to be bound by theory, it is believed that the pKa of the amine of the piperidine group—which is around pKa 8.1 at 25° C.—drops as the temperature increases during thermal sterilization, resulting in an increase in the amount of bupivacaine free base in solution. The hydrophobic free base adsorbs to the plastic inner surface of the container which increases the amount of residual HCl in solution leading to a reduction of the pH. The reduction of pH leads to re-protonation of the remaining free base in solution thereby limiting the adsorption of the free base to the plastic inner surface.

The term "thermal sterilization" as used herein refers to heat sterilization, preferably to moist heat sterilization. Preferably, moist heat sterilization is used with overheated water as sterilizing medium. The temperature of the overheated water is generally at least 100° C., preferably at least 110° C., more preferably at least 120° C. The pressure during thermal sterilization is generally at least 1 bar (100 kilopascal), for example at least 1.5 bar (150 kilopascal), at least 1.7 bar (170 kilopascal), at least 2 bar (200 kilopascal), at least 3 bar (300 kilopascal), or at least 4 bar (400 kilopascal). In some embodiments, the pressure during thermal sterilization is between 1 bar and 4 bar, e.g., 1-3 bar, 1.5-2 bar, 1.7-2 bar, or 1.7-3 bar. Thermal sterilization is generally carried out for at least 10 minutes, e.g., at least 12 minutes, at least 15 minutes, at least 17 minutes, or at least 20 minutes.

In some embodiments, the formulation of the invention is subject to thermal sterilization, which may be performed, e.g., as an intermediate step in the formulation process or as a final step in the formulation process. Performing thermal sterilization as a final step in the formulation process, e.g., after a bulk formulation is filled into a plurality of primary containers, is referred to herein as terminal sterilization. Additional steps may be carried out after terminal sterilization, e.g., placing thermally sterilized bags (e.g., where the formulation has been thermally sterilized while contained within bags used as primary containers) into a secondary overwrap, optionally adding an oxygen absorber, etc. Preferably, terminal sterilization refers to thermally sterilizing, e.g., autoclaving, a final dosage form already packaged in the primary container. Accordingly, as used herein, the term "thermal sterilization" includes terminal sterilization.

In some embodiments, the thermal sterilization of the formulation according to the present invention is carried out at a temperature of 120° C.-122° C. and a pressure of 2 bar (200 kilopascal) for 15-20 minutes. In certain embodiments, the thermal sterilization is carried out at a temperature of 121° C. and a pressure of 2 bar (200 kilopascal) for 15 minutes.

The formulation of the invention may include a pH adjuster. A suitable pH adjuster may include, for example, sodium hydroxide, potassium hydroxide, hydrochloric acid, or a combination thereof. In some embodiments, the pH adjuster includes sodium hydroxide, hydrochloric acid, or a combination thereof. The amount of pH adjuster included in a formulation of the invention may vary based upon the desired initial pH of the formulation. As used herein, the term "initial pH" refers to the pH of a bupivacaine formulation at the end of a compounding process and prior to thermal, e.g., terminal, sterilization. The initial pH can be measured in a bulk bupivacaine formulation prior to filling into an individual container (e.g., bag), or the initial pH can be measured in a bupivacaine formulation which has been filled into an individual container.

In some embodiments, the bupivacaine formulation may have an initial pH of about 4.0 or more, e.g., about 4.1 or more, about 4.2 or more, about 4.3 or more, about 4.4 or more, about 4.5 or more, or about 4.6 or more. In some embodiments, the formulation may have an initial pH of about 5.0 or less, e.g., about 4.9 or less, about 4.8 or less, about 4.7 or less, about 4.6 or less, about 4.5 or less, or about 4.4 or less. The invention also includes embodiments in which the bupivacaine formulation has an initial pH bounded by any two of the foregoing endpoints. For example, the bupivacaine formulation may have an initial pH of from about 4.0 to about 5.0, from about 4.0 to about 4.8, from about 4.1 to about 4.7, from about 4.1 to about 4.6, from about 4.2 to about 4.6, from about 4.2 to about 4.5, or from about 4.2 to about 4.4. In some embodiments, the formulation has a pH of about 4.3. In a preferred embodiment, the formulation has a pH of from about 4.2 to about 4.4, more preferably the formulation has a pH of about 4.3.

The formulation of the invention may be formulated to exhibit a low pH drift following terminal sterilization and/or storage at room temperature and/or under accelerated conditions. As used herein, the term "pH drift" refers to the amount of a change in pH of a formulation from a first pH, e.g., an initial pH, to a second pH, e.g., after terminal sterilization and/or storage. In some embodiments, the pH drift of the formulation is less than about 0.4 pH units, e.g., less than about 0.3 pH units, less than about 0.25 pH units, less than about 0.2 pH units, less than about 0.15 pH units, less than about 0.1 pH units, or less than about 0.05 pH units, following terminal sterilization. In some embodiments, the pH drift of the formulation is less than about 0.4 pH units, e.g., less than about 0.3 pH units, less than about 0.25 pH units, less than about 0.2 pH units, less than about 0.15 pH units, less than about 0.1 pH units, or less than about 0.05 pH units, following storage for at least about 6 months at room temperature. The invention also includes embodiments in which the pH drift of the formulation is less than about 0.4 pH units, e.g., less than about 0.3 pH units, less than about 0.25 pH units, less than about 0.2 pH units, less than about 0.15 pH units, less than about 0.1 pH units, or less than about 0.05 pH units, following storage for at least about 12 months at room temperature. In some embodiments, the pH drift of the formulation is less than about 0.4 pH units, e.g., less than about 0.3 pH units, less than about 0.25 pH units, less than about 0.2 pH units, less than about 0.15 pH units, less than about 0.1 pH units, or less than about 0.05 pH units, following storage for at least about 24 months at room temperature.

The formulation of the invention may include at least one tonicity agent. Suitable tonicity agents may include, without limitation, sodium chloride, dextrose, mannitol, trehalose, potassium chloride, glycerol, or a combination thereof. In some embodiments, the tonicity agent includes sodium chloride. In other embodiments, the tonicity agent includes dextrose. The tonicity agent is preferably present in an amount that renders the formulation isotonic. For example, the tonicity agent may present in an amount sufficient to provide the formulation with an osmolality of about 250-350 mOsm/kg, e.g., about 270-330 mOsm/kg, about 260-320 mOsm/kg, about 300-340 mOsm/kg, or about 310-330 mOsm/kg. In some embodiments, the tonicity agent is present in an amount that provides the formulation with an osmolality of about 290 mOsm/kg±10%. The invention also includes embodiments in which the formulation includes about 9 mg/mL dextrose.

The formulation additionally may include at least one buffer. In some embodiments, however, the formulation is free of a buffer, or substantially free of a buffer. If present, the type and amount of buffer present in the formulation may be selected based on several considerations, including but not limited to, for example, a target initial pH, pH stabilization, impurity formation, coloration, and/or patient tolerance upon administration. In some embodiments, the buffer may include a weak acid and a conjugate base of the weak acid. The weak acid and conjugate base may be added to the formulation in an anhydrous or hydrated form. In some embodiments, the conjugate base may be present in salt form. The invention also includes embodiments in which the acid or weak acid component may be a dicarboxylic acid or a tricarboxylic acid. For example, the acid includes citric acid, isocitric acid, aconitic acid, trimesic acid, propane-1,2,3-tricarboxylic acid, fumaric acid, oxalic acid, maleic acid, malonic acid, glutaric acid, succinic acid, tartaric acid, or a combination thereof.

One of ordinary skill in the art may readily determine the amount of buffer required to achieve or maintain a desired pH, for example, based upon a weak acid and conjugate base included in the formulation. In some embodiments, the buffer may be present at a concentration of about 50 mM or less, e.g., about 40 mM or less, about 30 mM or less, about 20 mM or less, about 10 mM or less, or about 5 mM or less. In some embodiments, the buffer may be present at a concentration of about 0.5 mM or more, e.g., about 1 mM or more, about 2 mM or more, about 5 mM or more, about 10 mM, or about 20 mM or more. The invention also includes embodiments in which a buffer is present at a concentration of about 0.5-40 mM, e.g., about 1-20 mM, about 2-12 mM, about 7-11 mM, or about 8-10 mM.

The formulation may further include at least one additional excipient. Non limiting examples of suitable excipients may include, for example, diluents, salts, stabilizers, solubilizers, antioxidants, preservatives, and the like, and combinations thereof. In some embodiments, however, the formulation is free of an additional excipient, or substantially free of an additional excipient.

The formulation may include at least one additional API (active pharmaceutical ingredient). Non limiting examples of suitable APIs include, for example, vasoconstrictors such as epinephrine, analgesics such as meloxicam, and anesthetics such as lidocaine. In some embodiments, however, the formulation is free of an additional API. In certain embodiments, the formulation does not contain epinephrine or a pharmaceutically acceptable salt thereof.

Thus, in certain embodiments, the invention provides a stable, ready-to-administer formulation consisting essentially of a therapeutically effective amount of bupivacaine or a pharmaceutically acceptable salt thereof, a tonicity agent, a pH adjuster, and water, wherein the formulation has an initial pH of from about 4.2 to about 4.5. In other embodiments, the invention provides a stable, ready-to-administer formulation consisting of, e.g., consisting exclusively of, a therapeutically effective amount of bupivacaine or a pharmaceutically acceptable salt thereof, a tonicity agent, a pH adjuster, and water, wherein the formulation has an initial pH of from about 4.2 to about 4.5.

The invention further provides a pharmaceutical product which includes a primary container with the ready-to-administer bupivacaine formulation of the invention contained therein. The liquid formulation component of the pharmaceutical product may include formulations having the same composition and characteristics (e.g., stability) as described herein with respect to the formulation of the invention. The primary container may include, for example, a syringe, a cartridge, a vial, an ampoule, a bag, or a bottle. In some embodiments, the primary container is a bag or a bottle. In certain embodiments, the primary container is glass, whereas in other embodiments the primary container is plastic.

The primary container may include, for example, a flexible, multi-layered bag. The bag may include a material which is chemically inert to the formulation, sterilizable, and weldable. Such materials may include, without limitation, polyolefin polymers (e.g., a polyethylene or polypropylene), cycloolefin polymers or cycloolefin copolymers, polycarbonates, styrene polymers, and block co-polymers thereof. In some embodiments, a polyolefin may be combined with an elastomeric polymer, such as, e.g., a styrene-ethylene/butylene-styrene-triblock polymer (SEBS), a styrene-ethylene/propylene-styrene-triblock polymer (SEPS), a styrene-butadiene-styrene-triblock polymer (SBS), and/or a styrene-isoprene-styrene triblock polymer (SIS). In some embodiments, the innermost layer of the multi-layered bag comprises a non-polar polymer. In certain embodiments, the innermost layer of the multi-layered bag comprises polypropylene and SEBS. In other embodiments, the innermost layer of the multi-layered bag comprises a polymer of cyclic olefin such as cycloolefin homopolymer or cycloolefin copolymer or mixture thereof. In yet other embodiments, the innermost layer of the multi-layered bag comprises ethylene-vinyl acetate copolymer. Suitable flexible bags are described in U.S. Pat. Nos. 5,783,269, 7,875,016, 8,162,915, 7,828,787, and/or 8,118,802, which are incorporated herein by reference in their entireties, and containers marketed under the tradename, FREEFLEX™. Other flexible polymeric containers suitable for use with a formulation according to the invention include, without limitation, GALAXY™, VIAFLO™, INTRAVIA™, and EXCEL™ containers.

In some embodiments, the primary container is disposed within and enclosed by a secondary container, such as, e.g., a blister package or an overwrap. The secondary container may include an overwrap with, e.g., a first foil, a second foil, and a seal disposed along a common peripheral edge of the first and second foils. The first and second foils of the secondary container overwrap may include multilayer films. In some embodiments, the secondary container is fully transparent to enable visual inspection of the primary container, labeling, and any other contents within the secondary container (e.g., oxygen absorber). The invention also includes embodiments in which the secondary container is fully intransparent, for example, an aluminum overpouch. The invention additionally includes embodiments in which the secondary container includes a completely or partially intransparent first foil and a completely or partially transparent second foil. Examples of secondary containers suitable for use in the present invention are described in US Patent Application Publication Nos. 2006/0240204 and 2019/0151202, which are incorporated herein by reference in their entireties.

The pharmaceutical product may further include an oxygen absorber that absorbs and removes or decreases the level of oxygen that may be present in the liquid bupivacaine formulation, in the headspace of the primary container, and/or within the secondary container after initial packaging, as well as oxygen that may permeate through the secondary container during the shelf life of the pharmaceutical product. The oxygen absorber may be provided in any suitable size, form, or shape including, for example, a sachet, pouch, capsule, label, strip, patch, canister, cartridge, lining, or sticker, etc. The oxygen absorber may be placed inside of the secondary container or adhered or integrated into the primary container and/or the secondary container. In some embodiments, the oxygen absorber may be in the form of a sachet or in the form of a canister. The pharmaceutical product of the invention also includes embodiments in which the oxygen absorber may be in the form of a label or in the form of a strip. The pharmaceutical product of the invention additionally includes embodiments in which the oxygen absorber may be in the form of a sticker or label that adheres to the secondary container or to the primary container. The pharmaceutical product of the invention further includes embodiments in which the oxygen absorber may be incorporated as part of the secondary container itself such as, for example, as part of a lid, film, or seal of the secondary container.

Suitable materials for oxygen absorbers may include, for example, metal-based substances that remove oxygen by reacting with it via chemical bonding, generally forming a metal oxide component. Metal-based substances may include, e.g., elemental iron as well as iron oxide, iron hydroxide, iron carbide, and the like, and combinations thereof. Other metals for use as oxygen absorbers may include, e.g., nickel, tin, copper, zinc, and combinations thereof. Metal-based oxygen absorbers may be provided in the form of a powder, e.g., to increase active surface area. Powder forms of suitable metal-based oxygen absorbers may be obtained by any known method including, but not limited to, atomization, milling, pulverization, and electrolysis. Additional materials for oxygen absorbers may include, e.g., low molecular weight organic compounds such as, e.g., ascorbic acid, sodium ascorbate, catechol and phenol, activated carbon, polymeric materials incorporating a resin and a catalyst, and combinations thereof. In some embodiments, the oxygen absorber includes a metal-based oxygen absorber, such as an iron-based oxygen absorber.

A formulation of the invention that includes a pharmaceutically effective amount of bupivacaine or a pharmaceutically acceptable salt thereof, a tonicity agent, a pH adjuster, and water may be prepared by any suitable technique, including formulation techniques which are known in the art. The formulation also may be prepared, e.g., in a batch or continuous process. In some embodiments, the formulation may be prepared by combining the components thereof in any order. The term "component" as used herein includes individual ingredients (e.g., bupivacaine hydrochloride, tonicity agent, pH adjuster, optional buffer, etc.) as well as any combination of two or more individual ingredients. In some embodiments, the formulation may be formed by combining the components together in a vessel. Such components may be combined in any order.

Thus, the invention provides a method for making/preparing a ready-to-administer, liquid bupivacaine formulation that is stable for at least 12 months at room temperature. In some embodiments, the method comprises dissolving a pharmaceutically effective amount of bupivacaine or a pharmaceutically acceptable salt thereof and a tonicity agent in water to form a first solution, adjusting the first solution to a pH of from about 4.2 to about 4.5 to form a second solution, and sterilizing the second solution to provide the ready-to-administer, liquid bupivacaine formulation. In some embodiments, the second solution is filtered and filled into a plurality of primary containers, such as bags, prior to sterilization.

In some embodiments, the method of the invention includes adding water to a suitable vessel, adding the tonicity agent, and stirring the mixture until dissolution is complete. Next, the bupivacaine or pharmaceutically acceptable salt thereof may be added, and the mixture stirred until dissolution is complete or substantially complete. In other embodiments, the order of addition and dissolution of the tonicity agent and bupivacaine or pharmaceutically acceptable salt thereof may be reversed. Subsequently, the pH may be adjusted to the desired value by adding one or more pH adjusters. Next, the volume of the formulation may be adjusted to a desired volume with water, filtered through one or more sterilizing filters, and filled into primary containers. Then, the primary container may be sealed and optionally placed into a secondary container, which may then be sealed. In some embodiments, an oxygen absorber may be placed into the secondary container before it is sealed. In certain embodiments, dissolved oxygen is removed, e.g., by nitrogen sparging, at one or more steps of the compounding, filling, and/or packaging processes.

In some embodiments, the sealed, pharmaceutical product is sterilized by thermal (e.g., terminal) sterilization. In some embodiments, the mixture is thermally sterilized prior to filing into individual containers.

The invention also provides a method of stabilizing a bupivacaine formulation by forming a mixture which includes bupivacaine or a pharmaceutically acceptable salt thereof, a tonicity agent, and water and adjusting the pH of the mixture to from about 4.2 to about 4.5, thereby stabilizing the formulation. The type/form and amounts of bupivacaine or pharmaceutically acceptable salt thereof and tonicity agent present in the mixture, as well as the pH, may include the same types/forms and amounts of these components and the pH described herein with respect to a formulation of the invention. The formulation produced by the inventive method may have the same stability characteristics as the stability characteristics described herein with respect to a formulation of the invention, particularly with regard to API assay and total impurities.

The formulation according to the invention is suitable for administration to a subject to induce anesthesia and/or provide analgesia. Preferably, the subject is a mammal such as, for example, a human.

In some embodiments, the invention provides a method of inducing or maintaining anesthesia in a patient comprising administering a stable, ready-to-administer bupivacaine formulation of the invention to the patient, thereby inducing or maintaining anesthesia in the patient. In other embodiments, the invention provides a method of providing analgesia to a patient comprising administering a stable, ready-to-administer bupivacaine formulation of the invention to the patient, thereby providing analgesia to the patient. In certain embodiments, the route of administration is epidural infusion.

EMBODIMENTS

1. A stable, ready-to-administer formulation comprising a therapeutically effective amount of bupivacaine hydrochloride, a tonicity agent, and water, wherein the formulation has an initial pH of from about 4.2 to about 4.5, and wherein the pH drift of the formulation is less than about 0.4 pH units following thermal sterilization.

2. The formulation of claim 1, wherein the bupivacaine hydrochloride is present at a concentration of about 0.625 mg/mL or about 1.25 mg/mL.

3. The formulation of embodiment 1 or embodiment 2, wherein the tonicity agent comprises sodium chloride, dextrose, mannitol, trehalose, potassium chloride, glycerol, or a combination thereof.

4. The formulation of any one of embodiments 1-3, wherein the tonicity agent is present in an amount sufficient to provide the formulation with an osmotic pressure of about 270-330 mOsm/kg.

5. The formulation of any one of embodiments 1-4, wherein the formulation is substantially free of a buffer.

6. The formulation of any one of embodiments 1-5, wherein the formulation does not contain epinephrine or a pharmaceutically acceptable salt thereof.

7. The formulation of any one of embodiments 1-6, wherein the formulation has a pH drift of less than about 0.2 pH units following storage for at least about 6 months at room temperature.

8. The formulation of any one of embodiments 1-7, wherein the formulation contains not more than about 0.1% total impurities as determined by a peak area percent method by high-performance liquid chromatography (HPLC) after storage for at least about 6 months at room temperature.

9. The formulation of any one of embodiments 1-8, wherein the thermal sterilization comprises terminal sterilization.

10. A flexible plastic container comprising the formulation of any one of embodiments 1-9.

11. The flexible plastic container according to embodiment 10, wherein the innermost layer of the container comprises polypropylene and/or a butadiene-styrene copolymer.

12. A stable, ready-to-administer formulation comprising about 0.625 mg/mL or about 1.25 mg/mL of bupivacaine hydrochloride, about 9 mg/mL of sodium chloride, and water, wherein the formulation has an initial pH of from about 4.2 to about 4.5, and wherein the pH drift of the formulation is less than about 0.4 pH units following terminal sterilization.

13. The formulation of embodiment 12, wherein the formulation is substantially free of a buffer.

14. The formulation of embodiment 12 or 13, wherein the formulation does not contain epinephrine or a pharmaceutically acceptable salt thereof.

15. The formulation of any one of embodiments 12-14, wherein the formulation has a pH drift of less than about 0.2 pH units following storage for at least about 6 months at room temperature.

16. The formulation of any one of embodiments 12-15, wherein the formulation contains not more than about 0.1% total impurities as determined by a peak area percent method by high-performance liquid chromatography (HPLC) after storage for at least about 6 months at room temperature.

17. A flexible plastic container comprising the formulation of any one of embodiments 12-16.

18. The flexible plastic container according to embodiment 17, wherein the innermost layer of the container comprises polypropylene and/or a butadiene-styrene copolymer.

19. A pharmaceutical product comprising a stable, ready-to-administer formulation comprising a therapeutically effective amount of bupivacaine hydrochloride, a tonicity agent, and water packaged in a flexible plastic container, wherein the formulation has an initial pH of from about 4.2 to about 4.5, and wherein the pH drift of the formulation is less than about 0.4 pH units following terminal sterilization of the pharmaceutical product.

The following examples further illustrate the invention but, of course, should not be construed as in any way limiting its scope.

Example 1

This example demonstrates the pH drift of ready-to-administer bupivacaine formulations in a flexible plastic container following terminal sterilization.

Samples containing 1.0 mg/mL bupivacaine, 8.0 mg/mL sodium chloride, and water for injection were adjusted to a target pH of 4.0, 4.3, 4.6, 5.0, or 5.4 with hydrochloric acid (HCl) and/or sodium hydroxide (NaOH), filled into bags having an innermost layer comprising polypropylene and a butadiene-styrene copolymer, and terminally sterilized by autoclaving at 121° C. for 15 minutes.

The pH of each exemplary formulation was measured before and after terminal sterilization (TS) and the results are summarized in Table 1.

TABLE 1

| Adjusted pH | pH before TS | pH after TS | Delta pH before and after TS |
|---|---|---|---|
| 4.0 | 4.00 | 3.90 | 0.10 |
| 4.3 | 4.29 | 4.05 | 0.24 |
| 4.6 | 4.66 | 4.19 | 0.47 |
| 5.0 | 5.0 | 4.25 | 0.75 |
| 5.4 | 5.42 | 4.29 | 1.13 |

Samples containing 1.25 mg/mL bupivacaine, 9.0 mg/mL sodium chloride, and water for injection were adjusted to a target pH of 4.1, 4.3, 4.5, 4.7, 5.0, or 5.4 with HCl and/or NaOH, filled into bags having an innermost layer comprising polypropylene and a butadiene-styrene copolymer, and terminally sterilized by autoclaving at 121° C. for 15 minutes.

The pH of each exemplary formulation was measured before and after TS and the results are summarized in Table 2.

TABLE 2

| Adjusted pH | pH before TS | pH after TS | Delta pH before and after TS |
|---|---|---|---|
| 4.1 | 4.1 | 4.0 | 0.10 |
| 4.3 | 4.31 | 4.1 | 0.21 |
| 4.5 | 4.50 | 4.2 | 0.30 |
| 4.7 | 4.70 | 4.2 | 0.50 |
| 5.0 | 4.96 | 4.3 | 0.66 |
| 5.4 | 5.37 | 4.3 | 1.07 |

The results described in this example demonstrate that the pH of bupivacaine formulations decreases following terminal sterilization in a flexible plastic container and that the amount of pH decrease is greater in bupivacaine formulations having a higher pH before terminal sterilization.

Example 2

This example demonstrates the stability of ready-to-administer bupivacaine formulations in a flexible plastic container following terminal sterilization.

Samples containing 0.625 or 1.25 mg/mL bupivacaine, 9.0 mg/mL sodium chloride, and water for injection were adjusted to a target pH of 4.3 or 4.5 with HCl and/or NaOH, filled into bags having an innermost layer comprising polypropylene and a butadiene-styrene copolymer, packaged into plastic overpouches, and terminally sterilized by autoclaving at 121° C. for 15 minutes.

The samples were placed into stability chambers under room temperature (250° C.±2° C./60% RH±5% RH) or accelerated temperature (400° C.±2° C./75% RH±5% RH) storage conditions for 1-6 months, and then analyzed by HPLC for bupivacaine content and total impurities.

The HPLC conditions were as follows:

Column: ACE C18; 150×4.6 mm; 3 μm

Mobile Phase A: dissolve 1.94 g potassium dihydrogen phosphate and 2.48 g dipotassium hydrogen phosphate in 1000 mL deionized water Mobile Phase B: acetonitrile (ACN)

Column temperature: 30° C.

Flow rate: about 1.0 mL/min

Injection volume: about 50 μL

Autosampler temperature: 20° C.

Detection: UV at 215 nm for related substances of bupivacaine

UV at 263 nm for bupivacaine assay

Separation mode: Gradient

| Time (min.) | % MP A | % MP B |
|---|---|---|
| 0.0 | 65 | 35 |
| 12.0 | 25 | 75 |
| 15.0 | 25 | 75 |

Run time: 15 minutes

Post time: 5 minutes

The results for bupivacaine content (Assay, % labeled) and total impurities (% bupivacaine) as determined by peak area percent method are summarized in Table 3.

TABLE 3

| | 25° C. | | | | 40° C. | | | |
|---|---|---|---|---|---|---|---|---|
| Sample | time | pH | Assay | Total Imp. | time | pH | Assay | Total Imp. |
| 0.625 mg/mL | 0 M | 4.2 | 99.5 | <0.05 | 1 M | 4.4 | 100.5 | <0.05 |
| bupi., pH 4.3 | 3 M | 4.3 | 98.0 | <0.05 | 3 M | 4.4 | 101.6 | 0.05 |
| | 6 M | 4.3 | 98.5 | <0.05 | 6 M | 4.4 | 102.5 | 0.15 |
| 0.625 mg/mL | 0 M | 4.3 | 100 | <0.05 | 1 M | 4.4 | 100.5 | <0.05 |
| bupi., pH 4.5 | 3 M | 4.3 | 98.0 | <0.05 | 3 M | 4.4 | 100.5 | <0.05 |
| | 6 M | 4.4 | 98.0 | <0.05 | 6 M | 4.4 | 101.5 | <0.05 |
| 1.25 mg/mL | 0 M | 4.1 | 99.0 | <0.05 | 1 M | 4.3 | 100.1 | <0.05 |
| bupi., pH 4.3 | 3 M | 4.2 | 98.0 | <0.05 | 3 M | 4.3 | 99.5 | <0.05 |
| | 6 M | 4.3 | 98.5 | <0.05 | 6 M | 4.4 | 100.0 | <0.05 |
| 1.25 mg/mL | 0 M | 4.2 | 99.5 | <0.05 | 1 M | 4.3 | 100.0 | <0.05 |
| bupi., pH 4.5 | 3 M | 4.2 | 97.5 | <0.05 | 3 M | 4.4 | 100.0 | <0.05 |
| | 6 M | 4.3 | 98.5 | <0.05 | 6 M | 4.4 | 102.0 | <0.05 |

The results of this example demonstrate that the exemplary bupivacaine formulations having pH 4.3 or 4.5 are stable with respect to pH, assay, and total impurities.

Example 3

This example demonstrates the stability of ready-to-administer bupivacaine formulations in a flexible plastic container following terminal sterilization.

Samples containing 0.625 or 1.25 mg/mL bupivacaine, 9.0 mg/mL sodium chloride, and water for injection were adjusted to a target pH of 4.1 with HCl and/or NaOH, filled into bags having an innermost layer comprising polypropylene and a butadiene-styrene copolymer, packaged into plastic overpouches, and terminally sterilized by autoclaving at 121° C. for 15 minutes.

The samples were placed into stability chambers under room temperature (250° C.±2° C./60% RH±5% RH) or accelerated temperature (40° C.±2° C./75% RH±5% RH) storage conditions for 1-6 months, and then analyzed by HPLC for bupivacaine content and total impurities. The HPLC conditions were as described in Example 2.

The results for bupivacaine content (Assay, % labeled) and total impurities (% bupivacaine) as determined by peak area percent method are summarized in Table 4.

TABLE 4

| | 25° C. | | | | 40° C. | | | |
|---|---|---|---|---|---|---|---|---|
| Sample | time | pH | Assay | Total Imp. | time | pH | Assay | Total Imp. |
| 0.625 mg/mL | 0 M | 4.1 | 98.36 | <0.05 | 1 M | 4.1 | 98.13 | <0.05 |
| bupi., pH 4.1 | 3 M | 4.0 | 96.5 | <0.05 | 3 M | 4.1 | 98.2 | <0.05 |
| | 6 M | 4.1 | 99.6 | <0.05 | 6 M | 4.2 | 103.0 | <0.05 |
| 1.25 mg/mL | 0 M | 4.0 | 99.65 | <0.05 | 1 M | 4.1 | 99.13 | <0.05 |
| bupi., pH 4.1 | 3 M | 4.0 | 97.1 | <0.05 | 3 M | 4.0 | 99.1 | <0.05 |
| | 6 M | 4.1 | 100.3 | <0.05 | 6 M | 4.1 | 103.5 | <0.05 |

The results of this example demonstrate that the exemplary bupivacaine formulations having pH 4.1 are stable with respect to pH, assay, and total impurities.

Example 4

This example demonstrates the long term stability of ready-to-administer bupivacaine formulations in a flexible plastic container.

A mixing tank was filled with water for injection, 0.625 or 1.25 mg/mL of bupivacaine hydrochloride was added, and the solution was mixed for at least 10 minutes. 9 mg/mL of sodium chloride was added, and the solution was mixed for at least 10 minutes. The pH was measured and, if outside of pH 4.2-4.5, then 1N HCl and/or 1N NaOH was added to adjust to target pH 4.3 with continuous mixing for at least 10 minutes. The solution was filtered through a 0.22 mm filter, filled into 100-mL FREEFLEX™ bags having an innermost layer comprising polypropylene and a butadiene-styrene copolymer, packaged into transparent polypropylene overpouches, and terminally sterilized by autoclaving at 121° C. and a pressure of 1.6 bar for 15 minutes.

Samples from three lots of bags of each bupivacaine concentration were placed into stability chambers under room temperature (250° C.±2° C./40% RH±5% RH) or accelerated (40° C.±2° C./NMT 25% RH) conditions. At time zero and following storage for 3-12 months, the formulations were analyzed for pH value by standard technique and for bupivacaine assay and total impurities by HPLC.

HPLC conditions for assay were as follows:

Column: Waters ACQUITY™ UPLC BEH C18 (50 mm×2.1 mm, 1.7 μm)

Mobile Phase (MP) A: 0.1% trifluoroacetic acid (TFA) in water

MP B: 0.1% TFA in acetonitrile (ACN)

Column temperature: 45±3° C.

Flow rate: 0.6 mL/min

Injection volume: 1.6 μL

Separation mode: Gradient

| Time (min.) | % MP A | % MP B |
|---|---|---|
| 0.0 | 80 | 20 |
| 1.2 | 80 | 20 |
| 2.0 | 55 | 45 |
| 2.5 | 80 | 20 |
| 3.5 | 80 | 20 |

Autosampler temperature: 25±3° C.
Detection: UV at 230 nm
Runtime: 3.5 minutes
HPLC conditions for total impurities were as follows:
Column: Phenomenex KINETEX™ C18 (100 mm×3.0 mm, 2.6 µm)
MP A: 0.97 g potassium dihydrogen phosphate and 1.24 g dipotassium hydrogen phosphate dissolved in 1 L water
MP B: mixture of 900 mL ACN and 100 mL water
Column temperature: 40° C.
Flow rate: 0.8 mL/min
Injection volume: 50 µL
Separation mode: Gradient

| Time (min.) | % MP A | % MP B |
|---|---|---|
| 0.0 | 82 | 18 |
| 10.0 | 16 | 84 |
| 15.0 | 16 | 84 |

Autosampler temperature: 8° C.
Detection: UV at 215 nm; reference wavelength 360 nm
Runtime: 15 minutes
The results for pH, bupivacaine content (Assay, % labeled), and total impurities (% bupivacaine) as determined by peak area percent method are summarized in Table 5 (room temperature storage) and Table 6 (accelerated storage). The amount of total impurities is the sum of 2,6-dimethylaniline and unspecified degradation products of bupivacaine above the reporting threshold of 0.06% according to International Council for Harmonisation of Technical Requirements for Pharmaceuticals for Human Use (ICH) Q3B3 (R2): Impurities in New Drug Products.

TABLE 5

| Lot # | pH | | | Assay (%) | | | Total Impurities (%) | | |
|---|---|---|---|---|---|---|---|---|---|
| ([bupi]) | t = 0 | t = 6 | t = 12 | t = 0 | t = 6 | t = 12 | t = 0 | t = 6 | t = 12 |
| 1 (0.625) | 4.3 | 4.4 | 4.3 | 97.5 | 96.5 | 99.4 | 0.0 | 0.0 | 0.0 |
| 2 (0.625) | 4.3 | 4.3 | 4.3 | 97.6 | 96.9 | 99.7 | 0.0 | 0.0 | 0.0 |
| 3 (0.625) | 4.3 | 4.3 | 4.3 | 96.1 | 97.4 | 99.2 | 0.0 | 0.0 | 0.0 |
| 4 (1.25) | 4.2 | 4.3 | 4.3 | 96.7 | 97.7 | 100.2 | 0.0 | 0.0 | 0.0 |
| 5 (1.25) | 4.2 | 4.3 | 4.3 | 97.3 | 97.9 | 99.5 | 0.0 | 0.0 | 0.0 |
| 6 (1.25) | 4.2 | 4.2 | 4.3 | 97.4 | 97.6 | 99.6 | 0.0 | 0.0 | 0.0 |

TABLE 6

| Lot # | pH | | | Assay (%) | | | Total Impurities (%) | | |
|---|---|---|---|---|---|---|---|---|---|
| ([bupi]) | t = 0 | t = 3 | t = 6 | t = 0 | t = 3 | t = 6 | t = 0 | t = 3 | t = 6 |
| 1 (0.625) | 4.3 | 4.3 | 4.4 | 97.5 | 100.1 | 102.1 | 0.0 | 0.0 | 0.0 |
| 2 (0.625) | 4.3 | 4.3 | 4.5 | 97.6 | 100.2 | 102.2 | 0.0 | 0.0 | 0.0 |
| 3 (0.625) | 4.3 | 4.3 | 4.3 | 96.1 | 100.6 | 99.9 | 0.0 | 0.0 | 0.0 |

TABLE 6-continued

| Lot # | pH | | | Assay (%) | | | Total Impurities (%) | | |
|---|---|---|---|---|---|---|---|---|---|
| ([bupi]) | t = 0 | t = 3 | t = 6 | t = 0 | t = 3 | t = 6 | t = 0 | t = 3 | t = 6 |
| 4 (1.25) | 4.2 | 4.3 | 4.4 | 96.7 | 100.4 | 101.9 | 0.0 | 0.0 | 0.0 |
| 5 (1.25) | 4.2 | 4.3 | 4.3 | 97.3 | 101.3 | 103.1 | 0.0 | 0.0 | 0.0 |
| 6 (1.25) | 4.2 | 4.3 | 4.4 | 97.4 | 102.4 | 102.0 | 0.0 | 0.0 | 0.0 |

The results of this example demonstrate that a ready-to-administer, liquid formulation of bupivacaine, a tonicity agent, and water having an initial pH of from 4.2 to 4.5 demonstrates excellent storage stability over at least 6 months at 40° C. or 12 months at room temperature.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical product comprising a stable, ready-to-administer formulation comprising an initial concentration of bupivacaine hydrochloride, a tonicity agent, and water packaged in a flexible plastic container wherein the innermost layer of the container comprises polypropylene, wherein the formulation is in the form of an aqueous solution and has an initial pH of from 4.3 to 4.5, wherein the pH drift of the formulation is less than 0.4 pH units following thermal sterilization of the pharmaceutical product, wherein the formulation is substantially free of a buffer and does not contain epinephrine or a pharmaceutically acceptable salt thereof, and wherein following storage of the container for at least about 6 months at room temperature, the formulation (1) has a pH drift of less than about 0.2 pH units, (2) contains from about 97% to about 103% of the initial concentration of bupivacaine, and (3) contains not more than about 0.1% total impurities as determined by a peak area percent method by high-performance liquid chromatography (HPLC).

2. The pharmaceutical product of claim 1, wherein the innermost layer of the container further comprises a butadiene-styrene copolymer.

3. The pharmaceutical product of claim 1, wherein the initial concentration is 0.625 mg/mL or 1.25 mg/mL of bupivacaine hydrochloride.

4. The pharmaceutical product of claim 1, wherein the tonicity agent comprises sodium chloride, dextrose, mannitol, trehalose, potassium chloride, glycerol, or a combination thereof.

5. The pharmaceutical product of claim 1, wherein the tonicity agent is present in an amount sufficient to provide the formulation with an osmotic pressure of about 270-330 mOsm/kg.

6. A pharmaceutical product comprising a stable, ready-to-administer formulation comprising an initial concentration of 0.625 mg/mL or 1.25 mg/mL bupivacaine hydrochloride, sodium chloride, and water packaged in a flexible plastic container wherein the innermost layer of the container comprises polypropylene and a butadiene-styrene copolymer, wherein the formulation is in the form of an aqueous solution and has an initial pH of from 4.3 to 4.5, wherein the pH drift of the formulation is less than 0.4 pH units following thermal sterilization of the pharmaceutical product, wherein the formulation is substantially free of a buffer and does not contain epinephrine or a pharmaceutically acceptable salt thereof and wherein following storage of the container for at least about 6 months at room temperature, the formulation (1) has a pH drift of less than about 0.2 pH units, (2) contains from about 97% to about 103% of the initial concentration of bupivacaine, and (3) contains not more than about 0.1% total impurities as determined by a peak area percent method by high-performance liquid chromatography (HPLC).

* * * * *